United States Patent [19]

Treon et al.

[11] Patent Number: 5,230,886
[45] Date of Patent: Jul. 27, 1993

[54] TUMOR CELL SUPPRESSION

[75] Inventors: Steven P. Treon, W. Roxbury; Selwyn A. Broitman, Newton Highlands, both of Mass.

[73] Assignee: Trustees of Boston University, Boston, Mass.

[21] Appl. No.: 853,132

[22] Filed: Mar. 18, 1992

[51] Int. Cl.$^5$ ............... A61K 45/00; A61K 37/66; A61K 37/02; A61K 37/04
[52] U.S. Cl. .................. 424/85.1; 424/85.4; 424/85.5; 424/85.6; 424/85.7; 424/88; 514/21
[58] Field of Search ............ 514/21; 424/85.1, 85.4, 424/85.5, 85.6, 85.7, 88

[56] References Cited

U.S. PATENT DOCUMENTS 4,851,219 7/1989 Sherwin.
4,863,727 9/1989 Zimmerman et al.

OTHER PUBLICATIONS

Spriggs, et al., "Recombinant Human Tumor Necrosis Factor Administered as a 24-Hour Intravenous Infusion. A Phase I and Pharmacologic Study", Sep. 7, 1988, J. Natl. Cancer Inst., vol. 80, pp. 1039-1044.
Creaven P., et al., "A Phase I Clinical Trial of Recombinant Human Tumor Necrosis Factor Given Daily for Five Days", 1989, Cancer Chemother. Pharmacol., vol. 23, pp. 186-191.
Lenk H., et al., "Phase II Clinical Trial of High-Dose Recombinant Human Tumor Necrosis Factor", 1989, Cancer Chemother. Pharmacol., vol. 24, pp. 391-392.
Demetri, G., et al., "A Phase I Trial of Recombinant Human Tumor Necrosis Factor and Interferon-Gamma: Effects of Combination Cytokine Administration In Vivo", Oct. 1989, Jour. Clin. Oncol., vol. 7, pp. 1545-1553.
Engelhardt, R., et al., "A Phase I Trial of Intravenously Administered Endotoxin", Mar. 1991, Proc. Am. Assoc. Cancer Res., vol. 32, p. 268, A1594.
Kunkel, S. L., et al., "Regulation of Macrophage Tumor Necrosis Factor Production by Prostaglandin $E_2$", 1986, Bioc. Biop. Res. Comm., vol. 137, pp. 404-410.
Karck, U., et al., "The Release of Tumor Necrosis Factor From Endotoxin-Stimulated Rat Kupffer Cells is Regulated by Prostaglandin $E_2$ and Dexamethasone", 1988, Jour. Hepat., vol. 7, pp. 352-361.
Levin S., et al., "Interferon System in Acute Viral Hepatitis", 1982, Lancet, vol. 1, pp. 592-594.
Treon, S. P., et al., "Demonstration of Concurrent Endotoxaemia and TNF-Aemia in Acute Viral Hepatitis Patients", 1991, Gastroenterology, vol. 100, p. A845.
Michie, H. R., et al., "Detection of Circulating Tumor Necrosis Factor After Endotoxin Administration", Jun. 9, 1988, New Eng. Jour. Med., vol. 318, pp. 1481-1486.

(List continued on next page.)

Primary Examiner—Michael G. Wityshyn
Assistant Examiner—Choon P. Koh
Attorney, Agent, or Firm—Choate, Hall & Stewart

[57] ABSTRACT

A method for treating a cancer includes administration of an endotoxin to a patient at least a portion of whose neoplastic cells express the CD14 surface receptor. The endotoxin can be administered concurrently or sequentially with a binding protein capable of binding the endotoxin and, for example, where the endotoxin is a lipopolysaccharide or a nontoxic portion of a lipopolysaccharide, it may for example be administered concurrently with a lipopolysaccharide binding protein. Also, the method including a step of first determining whether a portion of the patient's neoplastic cells express the CD14 surface receptor and, if not, administering to the patient prior to or concurrently with the endotoxin a cytokine. Also, a composition for treating a cancer, that includes an endotoxin in combination with at least one cytokine. Administration of the composition can provide more effective treatment of cancers than administration of a composition containing one or more cytokines alone. The method of the invention, and administration of the composition according to the invention can induce autocrine and paracrine suppression of growth by leukemic cells, and thus can be particularly effective for treatment of acute myelogenous leukemia.

14 Claims, No Drawings

OTHER PUBLICATIONS

Pelner, L., et al., "Effects of Concurrent Infections and Their Toxins on the Course of Leukemia", 1958, Acta Med. Scand., vol. 338 (Suppl) pp. 1–47.

Barton, J. C., "Beneficial Effects of Hepatitis in Patients with Acute Myelogenous Leukemia", 1979, Ann. Int. Med. vol. 90, pp. 188–190.

Barton, J. C., et al., "Prognostic Significance of Hepatitis in Acute Myelogenous Leukemia", 1979, Clin. Res., vol. 27, p. 490A.

Foon, K. A., et al., "Posttransfusion Hepatitis in Acute Myelogenous Leukemia", Oct. 17, 1980, JAMA, vol. 244, pp. 1806–1807.

Rotoli, B., et al., "Long-Term Survival in Acute Myelogenous Leukemia Complicated by Chronic Active Hepatitis", 1982, New Eng. Jour. Med., vol. 307, pp. 1712–1713.

Helson, L., et al., "Effect of Tumour Necrosis Factor on Cultured Human Melanoma Cells", Dec. 1975, Nature, vol. 258, pp. 731–732.

Peetre, C., et al., "Effects of Recombinant Tumor Necrosis Factor on Proliferation and Differentiation of Leukemic and Normal Hemopoietic Cells In Vitro", 1986, Jour. Clin. Invest., vol. 78, pp. 1694–1700.

Munker R., et al., "In Vitro Action of Tumor Necrosis Factor on Myeloid Leukemia Cells", Apr. 1987, Blood, vol. 69, pp. 1102–1108.

Sugarman, B. J., et al., "Recombinant Human Tumor Necrosis Factor-α: Effects on Proliferation of Normal and Transformed Cells In Vitro", Nov. 1985, Science, vol. 230, pp. 943–945.

Craig, R. W., et al., "Differentiation-Inducing and Cytotoxic Effects of Tumor Necrosis Factor and Interferon-Gamma in Myeloblastic ML-1 Cells", 1989, Jour. Cel. Physiol. vol. 141, pp. 46–52.

Haranaka, K., et al., "Antitumor Activity of Murine Tumor Necrosis Factor (TNF) Against Transplanted Human Tumors in Nude Mice", May 27, 1984, Int. Jour. Cancer, vol. 34, pp. 263–267.

Rothstein, J. L., et al., "Synergy Between Tumor Necrosis Factor and Bacterial Products Causes Hemorrhagic Necrosis and Lethal Shock in Normal Mice", 1988, Proc. Natl. Acad. Sci., USA, vol. 85, pp. 607–611.

Mannel, D. N., et al., "Macrophages as a Source of Tumoricidal Activity (Tumor-Necrotizing Factor)", 1980, Infect. Immun., vol. 30, pp. 523–530.

Aggarwal, B. B., et al., "Human Tumor Necrosis Factor", 1985, Jour. Biol. Chem., vol. 260, pp. 2345–2354.

Mohri, M., et al., "Effects of Lipopolysaccharide on Phospholipase A, Activity and Tumor Necrosis Factor Expression in HL-60 Cells", 1990, Jour. Immunol., vol. 144, pp. 2678–2682.

Tobias, P. S., et al., "Identification of a Lipid A Binding Site in the Acute Phase Reactant Lipopolysaccharide Binding Protein", 1989, Jour. Biol. Chem., vol. 264, pp. 10867–10871.

Wright, S. D., et al., "CD14, a Receptor for Complexes of Lipopolysaccharide (LPS) and LPS Binding Protein", 1990, Science vol. 249, pp. 1431–1433.

TUMOR CELL SUPPRESSION

BACKGROUND OF THE INVENTION

This invention relates to the therapeutic treatment of cancers.

In recent years investigators have begun treating cancers with cytokines. The cytokines, which include tumor necrosis factor, interferons, interleukins and various other factors, are a class of immunomodulatory proteins secreted by monocytes, macrophages, and lymphocytes in response to mitogens. Cytokines have demonstrated antiproliferative and cytotoxic effects on some malignant cell lines in vitro, necrosis of tumors in vivo in animal models, and therapeutic effects in some human clinical trials.

Tumor necrosis factor alpha ("TNFα") has been described as inhibiting the proliferation in vitro of human melanoma cells, primary myeloid cells, and of some but not all myeloid leukemia cell lines when added to the culture media (Helson et al., 1975, *Nature*, Vol. 258, pp. 731-732; Peetre et al., 1986, *Jour. Clin. Invest.*, Vol. 78, pp. 1694-1700; Munker et al., 1987, *Blood*, Vol. 69, pp. 1102-1108). Intravenous or intra-tumoral injection of murine TNFα has also been described as being toxic against both human and murine transplanted tumors in nude mice (Haranaka et al., 1984, *Int. Jour. Cancer*, Vol. 34, pp. 263-267).

The combination of TNFα and interferon gamma ("IFNγ") has been demonstrated to be more effective than either cytokine alone in suppressing tumor cell lines in vitro. Addition of TNFα and IFNγ together to culture media augmented their antiproliferative effects on a subset of murine and human tumor cell lines in vitro (Sugarman et al., 1985, *Science*, Vol. 230, pp. 943-945). Whereas addition of either TNFα or IFNγ alone to the culture media of the myeloid leukemia cell line, ML-1, stimulates differentiation, exposure of ML-1 to TNFα and IFNγ together resulted in cell death (Craig et al., 1989, *Jour. Cel. Physiol.*, Vol. 141, pp. 46-52).

The treatment of transplanted and of chemically induced tumors in mice with TNFα and IL-2 has been demonstrated to be more effective than the treatment of these tumors with just one of these cytokines (U.S. Pat. No. 4,863,727). Seven dogs that had spontaneous tumors, including melanomas, pharyngeal squamous cell carcinoma, mammary adenocarcinoma, and mast cell tumors, were treated with a combination of TNFα and IL-2. TNFα was administered by intravenous injection and IL-2 was administered subcutaneously to each of the seven dogs. Each dog showed some form of response, either in slowed disease progression or reduction of tumor mass.

Clinical trials have also examined the effectiveness of TNFα and IFNγ, administered as an overlapping continuous 24 hour IV infusion, in patients having various sarcomas and carcinomas. Two of 36 patients treated exhibited some response (Demetri et al., 1989, *Jour. Clin. Oncol.*, Vol. 7, pp. 1545-1553).

Clinical trials have shown IFNγ to be effective in treating chronic myelogenous leukemia (U.S. Pat. No. 4,851,219). When used to treat patients who are lodged in teh pre-blastic phase, IFNγ was found to suppress the progression of the disease in 6 of 14 patients.

Leukemia patients have been occasionally observed to undergo "spontaneous remission" when they contract a concurrent acute secondary infection (Pelner et al., 1958, *Acta. Med. Scand.*, Vol. 338 (Suppl), pp. 1-47). The contraction of hepatitis by patients having acute myelogenous leukemia has been observed to prolong survival (Barton et al., 1979, *Clin. Res.*, Vol. 27, pp. 490; Barton et al., 1979, *Ann. Int. Med.*, Vol. 90, pp. 188-190; Foon et al., 1980, *JAMA*, Vol. 244, pp. 1806-1807; Rotoli et al., 1982, *New Eng. Jour. Med.*, Vol. 307, pp. 1712-1713). The etiology remains unknown.

Bacterial infection can cause toxic shock owing to bacterial lipopolysaccharide endotoxins ("LPS"), and in extreme cases death results. Intravenous injection of endotoxin into normal individuals causes a brief increase of TNFα levels in plasma (Michie et al., 1988, *New. Eng. Jour. Med.*, Vol. 318, pp. 1481-1486). Additionally, although TNFα has low toxicity on normal cells when injected subcutaneously into pathogen free mice, it can cause lethal shock and hemorraghic necrosis of tissue when subcutaneously injected into mice concurrently with LPS. In contrast, mice given concurrent subcutaneous injections of IFNγ and LPS or IL-1 and LPS do not exhibit toxic effects (Rothstein et al., 1988, *Proc. Natl. Acad. Sci., USA*, Vol. 85, pp. 607-611).

Lipopolysaccharide has been described to induce release of TNFα from monocytes and macrophages in vitro when added to the culture media (Mannel et al., 1980, *Infect. Immun.*, Vol. 30, pp. 523-530) LPS is bound and opsonized by a lipopolysaccharide binding protein ("LBP") (Tobias et al., 1989, *Jour. Biol. Chem.*, Vol. 264, pp. 10867-10871). LBP is present in serum at low levels and is induced during an acute phase response to LPS injected into rabbits. The release of TNFα by macrophages may be in part mediated by binding of LPS/LBP to the CD14 cell surface receptor (Wright et al., 1990, *Science*, Vol. 249, pp. 1431-1433). In contrast to monocytes and macrophages, an acute myeloid leukemia cell line, HL60, releases TNFα in vitro in response to phorbol esters added to the culture media (Aggarwal et al., 1985, *Jour. Biol. Chem.*, Vol. 260, pp. 2345-2354), but not in response to LPS added to the culture media (Mohri et al., 1990, *Jour. Immunol.*, Vol. 144, pp. 2678-2682).

SUMMARY OF THE INVENTION

We have discovered that administration of an endotoxin, and the administration of an endotoxin either concurrently or sequentially with at least one cytokine, provides an effective treatment of cancers, that can be more effective than the administration of a composition containing one or more cytokines alone. This treatment induces autocrine and paracrine suppression of growth by leukemic cells, and thus it can be particularly effective for acute myelogenous leukemia.

In one aspect the invention provides a method for therapeutic treatment of cancers in patients whose leukemia cells or other tumor cells, hereafter referred to as "neoplastic cells", are expressing the CD14 cell surface receptor by administering an endotoxin to the patient. "Therapeutic treatment", as used herein, is defined as providing beneficial treatment of disease. "Cancer", as used herein, means any of various types of malignant neoplasms, including for example carcinomas, leukemias, lymphomas, melanomas, and sarcomas. "Endotoxin" includes any of the complex phospholipid-polysaccharide macromolecules, for example lipopolysaccharide, which form an integral part of the cell wall of a variety of relatively avirulent as well as virulent strains of Gram-negative bacteria.

In preferred embodiments the endotoxin is lipopolysaccharide ("LPS"), or more preferably a non-toxic derivative of LPS, such as mono-phosphoryl lipid A. In some embodiments the endotoxin includes a combination of LPS and lipopolysaccharide binding protein ("LBP"). LPS is preferably purified from *Salmonella minnesota* or *Escherichia coli* 0111. LBP is preferably a recombinant human protein.

In another aspect the invention also provides for therapeutic treatment of cancers in patients whose neoplastic cells do not express the CD14 cell surface receptor, by inducing CD14 receptor expression by administering an endotoxin and at least one cytokine to the patient, and thereafter administering an endotoxin. "Cytokine" includes any of the serum soluble factors, produced by monocytes, macrophages, and lymphocytes in response to specific antigens, which are cytotoxic to cells. Cytokines can be released by sensitized cells on contact with a specific antigen, and help to effect cellular immunity by stimulating the activity of monocytes, macrophages, and lymphocytes.

In preferred embodiments the cytokine is preferably at least one of tumor necrosis factor alpha ("TNF$\alpha$"), tumor necrosis factor beta ("TNF$\beta$"), interferon alpha ("IFN$\alpha$"), interferon beta ("IFN$\beta$"), interferon gamma ("IFN$\gamma$"), interleukin-1 ("IL-1"), interleukin-6 ("IL-6"), and/or interleukin-8 ("IL-8"). The cytokines are preferably recombinant human proteins.

In preferred embodiments the endotoxin and the cytokines can be administered concurrently or sequentially. When administered sequentially, the cytokines are preferably administered prior to the endotoxin. "Concurrent" administration, as used herein, is defined as administering the substances to the subject beginning at the same time. "Sequentially", as used herein, is defined as administering the substances to the subject separately in a series such that the effects of the first substance administered remains in the patient when the last substance is administered.

In preferred embodiments endotoxin and cytokine are administered either intravenously or parenterally, and they can conveniently be administered by the same route. The treatment most preferably includes LPS, TNF$\alpha$, and IFN$\gamma$, in therapeutically effective amounts, and is administered by continuous infusion.

In another aspect the invention provides a composition, suitable for treatment of cancers that includes an endotoxin and at least one cytokine in therapeutically effective amounts. A "therapeutically effective" concentration of endotoxin and cytokines as used herein means a concentration of each substance that in combination provides beneficial treatment of disease.

In preferred embodiments the composition includes therapeutically effective amounts of an endotoxin, preferably lipopolysaccharide ("LPS"), or more preferably a non-toxic derivative of LPS, such as monophosphoryl lipid A, and at least one cytokine. In some embodiments, the endotoxin includes a combination of LPS and lipopolysaccharide binding protein ("LBP") in therapeutically effective concentrations.

In preferred embodiments the composition includes endotoxin, endotoxin binding protein, and cytokine in amounts that provide at least physiologically attainable concentrations in the patient. A "physiologically attainable" concentration, as used herein, approximates that which can be found in vivo when the human body has been infected with viruses including viral hepatitis, 107-150 U/ml IFN, 4-30 U/ml TNF$\alpha$, and 1-10 ng/ml LPS (Levin et al., 1982, *Lancet*, Vol. 1, pp. 592-594; and Treon et al., 1991, *Gastroenterology*, Vol. 100, p. A845), when stimulated with LPS to release TNF$\alpha$, 240 +/− 70 pg/ml TNF$\alpha$ (Michie et al., 1988, *New. Eng. Jour. Med.*, Vol. 318, pp. 1481-1486), or in normal human serum, 0.2–0.5 $\mu$g/ml LBP (Wright et al., 1990, *Science*, Vol 249, pp. 1431-1433).

DESCRIPTION OF THE PREFERRED EMBODIMENTS

The administration of an endotoxin, or an endotoxin with at least one cytokine, can provide an effective combination for the therapeutic treatment of cancer. The examples following illustrate treatment of acute myelogenous leukemia according to the invention.

Acute myelogenous leukemia is a disease with several subtypes classified as M1 through M7. Each subtype is identified by the relative state of differentiation of its cells, with M1 class cells being the least differentiated and M7 class cells the most differentiated.

Method

By way of example three different subtypes of acute myelogenous leukemia cell lines were exposed to cytokines and endotoxin in vitro and the effects are described. The examples are presented for illustrative purposes only. As will be appreciated, the method according to the invention can be used for the treatment of cancers in humans and other endotoxins or cytokines can be used according to the invention.

Generally, human myelogenous leukemic cell lines, KG1 (M1 class), HL60 (M2 class) and U937 (M4 class), were treated by adding varying combinations and amounts of LPS, TNF$\alpha$, and IFN$\gamma$ to the culture medium.

Particularly, the cells were cultured at $1 \times 10^6$ cells/ml, HL60 and U937 cells in RPMI 1640, 10% fetal bovine serum, streptomycin and penicillin, and KG1 cells in DMEM, 20% fetal bovine serum, glutamine, streptomycin and penicillin, and passaged every 3 days in fresh medium for 9 days; total cell count and viability were determined at each passage. The cells were treated with *Salmonella minnesota* LPS, recombinant human TNF$\alpha$ and recombinant human IFN$\gamma$.

EXAMPLE 1

Release of endogenous TNF$\alpha$ by HL60 cells after LPS stimulation

HL60 cells were cultured with 10 or 50 U/ml TNF$\alpha$, or combined TNF$\alpha$/IFN$\gamma$ (10 U/ml/100 U/ml or 50 U/ml/100 U/ml), for 6 and 9 days. Cells were then centrifuged at 300 g for 10 minutes, washed 3 times in RPMI and resuspended in RPMI at $1 \times 10^6$ cells/ml, and divided into sets. Half of the sets were stimulated for 6 hours with 1 $\mu$g/ml LPS. After stimulation the cells were centrifuged again as before and evaluated for TNF$\alpha$ release by cytotoxicity assay using TNF$\alpha$ sensitive WEHI 164-13 cells. Cells that were treated with either TNF$\alpha$ or TNF$\alpha$/IFN$\gamma$ and not stimulated with LPS did not release detectable levels of TNF$\alpha$ (<0.01 U TNF$\alpha$). Cells that were treated with TNF$\alpha$ and stimulated with LPS released low levels of TNF$\alpha$ (0.02–0.025 U TNF$\alpha$ released on day 6). Cells which were treated with combined TNF$\alpha$/IFN$\gamma$ and stimulated with LPS were induced to release significantly higher levels of TNF$\alpha$ (1.57–1.63 U TNF$\alpha$ on day 6). These results show that the combined effect of TNF$\alpha$-

/IFNγ/LPS on HL60 cells is superior to the effect of TNFα/IFNγ, as measured by TNFα release. That is TNFα/IFNγ function synergistically with LPS to elicit TNFα release.

EXAMPLE 2

Effects of LPS, TNFα and IFNγ treatment on HL60 cell growth, viability and differentiation.

HL60 cells were cultured for 3, 6, and 9 days in the presence of 10 U/ml TNFα, 100 U/ml IFNγ, 10 ng/ml LPS individually and in the following combinations: TNFα/LPS, IFNγ/LPS, TNFα/IFNγ, TNFα/IFNγ/LPS. Increased LPS concentrations of 100 ng/ml and 1000 ng/ml were additionally tested. In comparison to untreated cells, treatment with any of the substances alone resulted in decreases in cell growth and viability, treatment with combinations of any two of the substances produced slightly greater decreases in cell growth and viability. Treatment of HL60 cells with a combination of all three substances resulted in a significant decrease in cell growth and viability. Increasing concentrations of LPS enhanced this result.

The TNFα/IFNγ/LPS treated cells additionally showed an increase in monocytic path differentiation, as assessed by increased alpha-naphthyl acetate esterase expression, CD14 expression and changes in the microtubular network of the cytoskeleton.

The extent of growth inhibition, reduced viability, and differentiation of this acute myelogenous leukemia cell line due to the combined effects of TNFα/IFNγ/LPS, as compared to the other growth conditions tested, indicates that these substances together produce greater than additive effects. That is the inhibition of growth, decrease in viability and increase in differentiation resultant from treatment with TNFα/IFNγ/LPS is greater than the sum of the effects of any one pair.

EXAMPLE 3

Effects of LPS, TNFα and IFNγ treatment on KG1 and U937 cell growth, viability, and differentiation KG1 and U937 cells were cultured for 3, 6, and 9 days in the presence of TNFα, IFNγ, and LPS as described in example 2. A comparison of treated and untreated cells showed that treatment of cells with any of the substances alone resulted in significant decreases in cell growth and viability. However, treatment with TNFα/IFNγ/LPS did not result in statistically lower cell counts or viability than treatment with TNFα/IFNγ, and neither the KG1 nor U937 cell lines released TNFα after LPS stimulation.

Neither cell line could be scored for differentiation by alpha-naphthyl acetate esterase staining as no staining was seen in either treated or untreated KG1 cells and greater than 95% of untreated U937 cells were positive. The U937 cells, but not the KG1 cells, showed a reorganization of the microtubular network.

EXAMPLE 4

Paracrine mediated suppression of HL60 cells by release of endogenous TNFα.

Untreated HL60 cells were co-cultured with HL60 cells that had been pretreated by culturing with 10 U/ml TNFα/100 U/ml IFNγ for 6 days and then stimulated with LPS. Cells were co-cultured on either side of a 0.4 micron membrane. As a control for TNFα release, a neutralizing anti-TNFα antibody was added to sets of the co-cultured cells.

A significant decrease in viability of the untreated co-cultured cells was seen on day 3 when the cells were co-cultured with LPS-stimulated, TNFα/IFNγ pretreated cells as compared to cells which were co-cultured either with non-LPS-stimulated TNFα/IFNγ pretreated cells or with LPS stimulated TNFα/IFNγ pretreated cells in the presence of the anti-TNFα antibody. This decrease in viability by co-culturing untreated cells with LPS/TNFα/IFNγ treated cells demonstrates that the HL60 cells can have a paracrine effect upon one another.

The above described examples demonstrate that class M2 (HL60) and perhaps class M3 AML cells can be effectively treated with the combination of LPS/TNFα/IFNγ.

EXAMPLE 5

Expression of the CD14 receptor on the surface of HL60, KG1, and U937 cells

We have demonstrated in the treatments of different classes of AML cells above that M2 class AML cells (HL60) can be induced to release TNFα if the cells are treated with TNFα and IFNγ in addition to LPS. We further investigated the ability of AML cells to release TNFα after treatment with TNFα and IFNγ in a separate line of treatments which examined the expression of the CD14 receptor upon the surface of HL60, KG1 and U937 cells.

The CD14 receptor is not found on the surface of untreated HL60, KG1 or U937 cells. Treatment of HL60 cells with LPS/TNFα/IFNγ induces the expression of CD14 upon the surface of these cells to a greater extent than treatment with TNFα/IFNγ; approximately 63% of LPS/TNFα/IFNγ treated HL60 cells expressed CD14 as compared to about 15% of TNFα/IFNγ treated cells. In contrast the CD14 receptor was not expressed on the surface of LPS/TNFα/IFNγ treated KG1 or U937 cells.

Without being limited thereby, we here propose a theory for how the CD14 receptor is involved in the remission of leukemia.

Infection of a patient with viral hepatitis causes damage to the liver and results in incomplete clearance of LPS from the blood. The circulating LPS can induce the release of cytokines by the immune system, release of TNF and interferons has been measured, and this response of the immune system to the infection helps to lead to recovery of the hepatitis patient. It can be hypothesized that the contraction of post-transfusional hepatitis by leukemia patients will also induce the immune system to release cytokines and perhaps in some instances lead to remission of the leukemia. We have shown, however, that not all AML cells will release cytokines in response to LPS, and more specifically we have demonstrated that M2 class AML cells (HL60) release cytokines after induction of expression of the CD14 receptor by treatment of the HL60 cells with endotoxin and cytokines.

Based upon our results we propose that the expression of the CD14 receptor on the surface of leukemia cells may be necessary for them to secrete cytokines in response to treatment with LPS. This proposal is supported by the work of Wright et al. (1990) that described the binding of the LPS-LBP complex to the CD14 receptor to elicit the release of TNFα by macrophages. Expression of the CD14 receptor may also play a role in the observed paracrine repression of AML cells by one another.

Moreover, the responsiveness of a patient to treatment may be correlated to expression of the CD14 receptor by their leukemia cells. Although the treatment of cancer patients with cytokines is established in the art, a method for inducing a patients' leukemia cells, and perhaps other cancer cells, to secrete cytokines has not been proposed.

We have developed a therapeutic treatment that can induce leukemia cells and other tumor cells to secrete cytokines. A combination of cytokines is used to elicit the expression of the CD14 receptor on the neoplastic cell surface and LPS is used to stimulate the release of cytokines. A patient having neoplastic cells that express the CD14 receptor may alternatively respond to treatment with LPS, or LPS/LBP, and may not require additional treatment with cytokines.

Use

The method according to the invention can be used to treat cancers, including acute myelogenous leukemia. Treatment according to the invention may be effective in causing autocrine and paracrine suppression of acute myelogenous leukemia, and may also cause the necrosis of tumors in vivo.

In patients having leukemia their complete blood count can be monitored, and in patients having other cancers a sample of the tumorous tissue can be taken, prior to the first cycle of therapy and after each cycle of therapy to determine the expression of the CD14 receptor on the sampled cells. The complete blood count, and the tissue sample, would establish the expression the CD14 receptor on the surface of leukemia cells, or on the surface of other tumor cells. The use of FACS analysis with the appropriate antibody, such as anti-Leu M3 (available from Becton-Dickinson), can identify the expression of the CD14 receptor on the surface of neoplastic cells, and the endogenous production of TNFα by leukemia cells can be detected using a TNFα ELISA assay (available from Endogen). In patients having leukemia, the progress of the disease can also be followed by periodic aspiration of bone marrow.

Dosage regimes should be adjusted according to the response of the particular subject being treated, according to protocols generally recognized in clinical oncology (see Creaven et al., 1989, Cancer Chem. Pharm., Vol. 23, pp. 186–191; Demetri et al., 1989, Jour. Clin. Onc., Vol. 7, pp. 1545–1553; Spriggs et al., 1988, JNCI, Vol. 80, pp. 1039–1044; Lenk et al., 1989, Cancer Chem. Pharm., Vol. 24, pp. 391–2).

A cancer patient, especially a leukemia patient having expression of CD14 on the surface of their blood, or leukemia, cells or a cancer patient having expression of CD14 on the surface of their tumor cells, can be treated with LPS, or LPS and LBP. The following guidelines are suggested.

Patients to be treated should be given a prophylactic such as indomethacin approximately four hours prior to treatment with the cytokines and endotoxin. Prophylactic treatment can attenuate the symptoms of treatment and may also potentiate the release of endogenous cytokines (Karck et al., 1988, Jour. Hepat., Vol. 7pp. 352–361; Kunkel et al., 1986, Bioc. Biophys. Res. Comm., Vol. 137, pp. 404–410). Indomethacin dosage should start at 50 mg orally 3 times per day during treatment and increase to 4 times per day as needed to control fever. The prophylactic treatment should also continue for at least 48 hours after completion of the infusion of endotoxin (LPS), or LPS and LBP. Prophylactic treatment can result in bleeding diathesis and dosages should be decreased or therapy discontinued if active bleeding develops.

A patient can be administered an infusion of LPS (1–5 ng/kg in normal saline), or an infusion of LPS and LBP (LBP sufficient to provide a serum concentration of 0.2–0.5 $\mu$g/ml) over 24–72 hours. A patient should be monitored at least every 2 hours for temperature, blood pressure and urinary output, and observed for the development of high fever, hypotension, septic shock, or disseminated intravascular coagulation. Therapy should be discontinued if a patient develops a fever over 103.9° F., hypotension of SBP <90 mm Hg, anuria, or severe thrombocytopenia (platelet count <20,000 mm$^3$).

A patient can undergo repeated infusions of LPS, or LPS/LBP, as outlined above (1–6 treatments per month) as tolerated. Before and after each treatment the patient should be checked for evidence of hepatotoxicity and renal toxicity. The weight of each patient should be closely monitored for signs of fluid retention and cachexia, and an appetite stimulant can be given for a diminished appetite.

A leukemia patient whose complete blood count did not demonstrate expression of the CD14 receptor on the surface of the blood cells, or a patient with another cancer whose tumorous tissue sample did not demonstrate the expression of the CD14 receptor on the surface of the tumor cells, can be treated with a composition including an endotoxin and at least one cytokine. For example, a composition including LPS, TNFα, and IFNγ could be administered to a patient following treatment with a prophylactic, as described above, and monitoring of the patients response to the treatment. The following guidelines are suggested.

Recombinant IFNγ (200–4000 $\mu$g/m$^2$ in normal saline) can be administered by continuous infusion over 12 hours followed by the infusion of recombinant TNFα (136–683 $\mu$g/m$^2$ in normal saline) over the next 24 hours. During the infusion of IFNγ and TNFα patients should be observed for the development of hypotension, septic shock, disseminated intravascular coagulation, and high fever. The prophylactic treatment can help to control the fever that results from treatment with cytokines, however it can also result in bleeding diathesis and dosages should be decreased or therapy discontinued if active bleeding develops. Blood pressure, temperature and urinary output should be monitored at least every 2 hours and therapy should be discontinued if a fever over 103.9° F. develops, or if blood pressure decreases to SBP <90 mm Hg, or if anuria develops, or if severe thrombocytopenia develops (platelet count <20,000 mm$^3$).

If the patients condition is stable after treatment with the cytokines then infusion of LPS (1–5 ng/kg in normal saline), or an infusion of LPS and LBP (LBP sufficient to provide a serum concentration of 0.2–0.5 $\mu$g/ml) can be initiated and carried out over the next 24–72 hours. The patients should be monitored at least every 2 hours for temperature, blood pressure and urinary output, and observed for the development of high fever, hypotension, septic shock, or disseminated intravascular coagulation. Therapy should be discontinued if a patient develops a fever over 103.9° F., hypotension of SBP <90 mm Hg, anuria, or severe thrombocytopenia.

Patients can also be treated with IFNγ, TNFα, and LPS concurrently. A patient to be treated with the substances concurrently would be given the prophylactic treatment as discussed above, and treated by continuous infusion over 24-72 hours with the combination of the substances, preferably the concentration of each substance would be selected from the lower end of each range identified above. A patients blood pressure, temperature, and urinary output should be monitored at least every 2 hours and therapy should be discontinued if any of the above-discussed symptoms should occur.

Patients can undergo repeated infusions of IFNγ, TNFα, and LPS as outlined above (1-6 cycles per month) as tolerated. Before and after each cycle of treatment the patient should be checked for evidence of hepatotoxicity and renal toxicity. The weight of the patient should be closely monitored for signs of fluid retention and cachexia, and an appetite stimulant can be given for a diminished appetite. Additionally, a patient can be monitored for the induction of the expression of the CD14 receptor on the surface of the blood cells or tumor cells, and therapy can be continued with LPS, or LPS/LBP as described above.

Expression of the CD14 receptor

Patients, either with AML or other cancers, that are not responding to the treatment with IFNγ, TNFα and LPS may also not demonstrate an increase in the expression of the CD14 receptor. In these cases alternative cytokines, such as TNFβ, IFNα, IFNβ, IL-1, IL-6, and IL-8, can be used in order induce the expression of the CD14 receptor, and then treatment can be continued with IFNγ, TNFα and LPS. Determination of which cytokines are effective for inducing the expression of the CD14 receptor can be conducted by taking blood, or tumor cells, from the patient, isolating the cells, adding various combinations of cytokines with LPS, or LBP/LPS, to the wells, and assaying for expression of the CD14 receptor on the surface of the cells and for release of endogenous cytokines. Combinations of cytokines that effectively induce expression of the CD14 receptor can then be used to treat the patient in conjunction with endotoxin or endotoxin and its binding protein to induce autocrine and paracrine suppression of growth.

We claim:

1. A method for treating a cancer in a patient, comprising the steps of determining whether at least a portion of the patient's neoplastic cells express the CD14 surface receptor, and administering to the patient a therapeutically effective amount of an endotoxin.

2. The method of claim 1, further comprising administering to the patient an endotoxin binding protein.

3. The method of claim 1, further comprising, where said determining step results in a determination that the patient's neoplastic cells do not include cells that express the CD14 receptor, the step of administering to the patient a therapeutically effective amount of a cytokine.

4. The method of claim 3 wherein the cytokine administering step and the endotoxin administering step are carried out at least in part concurrently.

5. The method of claim 3 wherein the cytokine administering step and the endotoxin administering step are carried out sequentially.

6. The method of claim 3 wherein the cytokine administering step is initiated before the endotoxin administering step is initiated.

7. The method of claim 1 wherein the endotoxin administering step comprises administering to the patient a non-toxic derivative of a lipopolysaccharide.

8. The method of claim 3 wherein the cytokine administering step comprises administering a cytokine selected from the group consisting of tumor necrosis factor α, tumor necrosis factor β, interferon α, interferon β, interferon γ, interleukin-1, interleukin-6, and interleukin-8.

9. The method of claim 3 wherein the cytokine administering step comprises administering tumor necrosis factor α and administering interferon γ.

10. The method of claim 9 wherein the tumor necrosis factor α administering step and the interferon γ administering step are carried out at least in part concurrently.

11. The method of claim 8 wherein the endotoxin administering step comprises administering the endotoxin parenterally.

12. The method of claim 8 wherein the endotoxin administering step comprises administering the endotoxin by infusion.

13. The method of claim 3 wherein the cytokine administering step comprises administering the cytokine parenterally.

14. The method of claim 3 wherein the cytokine administering step comprises administering the cytokine by infusion.

* * * * *

UNITED STATES PATENT AND TRADEMARK OFFICE
CERTIFICATE OF CORRECTION

PATENT NO. : 5,230,886
DATED : July 27, 1993
INVENTOR(S) : Steven P. Treon, et al It is certified that error appears in the above-indentified patent and that said Letters Patent is hereby corrected as shown below:

Column 1, line 64: please delete "teh" and insert therefor -- the --; and

Column 8, line 57: please delete "patients" and insert therefor -- patient's --.

Signed and Sealed this

Fifth Day of July, 1994

*Attest:*

BRUCE LEHMAN

*Attesting Officer*  *Commissioner of Patents and Trademarks*